(12) United States Patent
Kemp et al.

(10) Patent No.: US 8,758,304 B2
(45) Date of Patent: Jun. 24, 2014

(54) AUTO-INJECTOR

(75) Inventors: Thomas Mark Kemp, Ashwell (GB); Matthew Ekman, Cheshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/877,160

(22) PCT Filed: Oct. 6, 2011

(86) PCT No.: PCT/EP2011/067490
§ 371 (c)(1),
(2), (4) Date: Jul. 16, 2013

(87) PCT Pub. No.: WO2012/045829
PCT Pub. Date: Apr. 12, 2012

(65) Prior Publication Data
US 2013/0289490 A1    Oct. 31, 2013

Related U.S. Application Data

(60) Provisional application No. 61/432,262, filed on Jan. 13, 2011.

(30) Foreign Application Priority Data

Oct. 8, 2010    (EP) .................................... 10186991

(51) Int. Cl.
 *A61M 5/32*    (2006.01)
(52) U.S. Cl.
 USPC ....................................................... 604/198
(58) Field of Classification Search
 USPC ....................................................... 604/198
 See application file for complete search history.

(56) References Cited

U.S. PATENT DOCUMENTS

2006/0287630 A1 * 12/2006 Hommann .................... 604/130

FOREIGN PATENT DOCUMENTS

EP    1728529 A1    12/2003
EP    1728529 A1 *  12/2006

(Continued)

*Primary Examiner* — Jason Flick
(74) *Attorney, Agent, or Firm* — McDonnell Boehnen Hulbert & Berghoff LLP

(57) ABSTRACT

The invention relates to an auto-injector for administering a dose of a liquid medicament, comprising:
 an elongate housing, a syringe with a hollow needle and a bung for displacing the medicament, wherein the syringe is slidably arranged with respect to the housing,
 spring means for pushing the needle from a covered position inside the housing into an advanced position past the proximal end and for supplying the dose of medicament,
 activating means for locking and releasing the spring means.

The spring means is a torsion spring grounded at one end in the housing and at the other end in a lead nut rotatable about a longitudinal axis but axially constrainable. The lead nut is arranged for translatively moving a piston rod by means of a lead screw thread. The piston rod is prevented from rotating relative to the housing and arranged to be coupled to the bung in order to push it forwards. The lead nut is engaged to the housing in an initial position prior to manual operation of the activating means in a manner to prevent rotation and disengaged from the housing by the activating means upon manual operation.

The activating means is a trigger button, arranged at a distal end of the housing. Prior to manual operation the trigger button, the piston rod and the lead nut are coupled for joint translation in proximal direction. In the initial position the lead nut is engaged to the housing by at least one spline feature. The lead nut is arranged to disengage from the housing on translation in proximal direction from the initial position.

11 Claims, 7 Drawing Sheets

(56) References Cited

FOREIGN PATENT DOCUMENTS

| WO | 0217996 A1 | 3/2002 |
| WO | 2009007305 A1 | 1/2009 |
| WO | WO 2009007305 A1 * | 1/2009 |
| WO | 2009037141 A1 | 3/2009 |

* cited by examiner

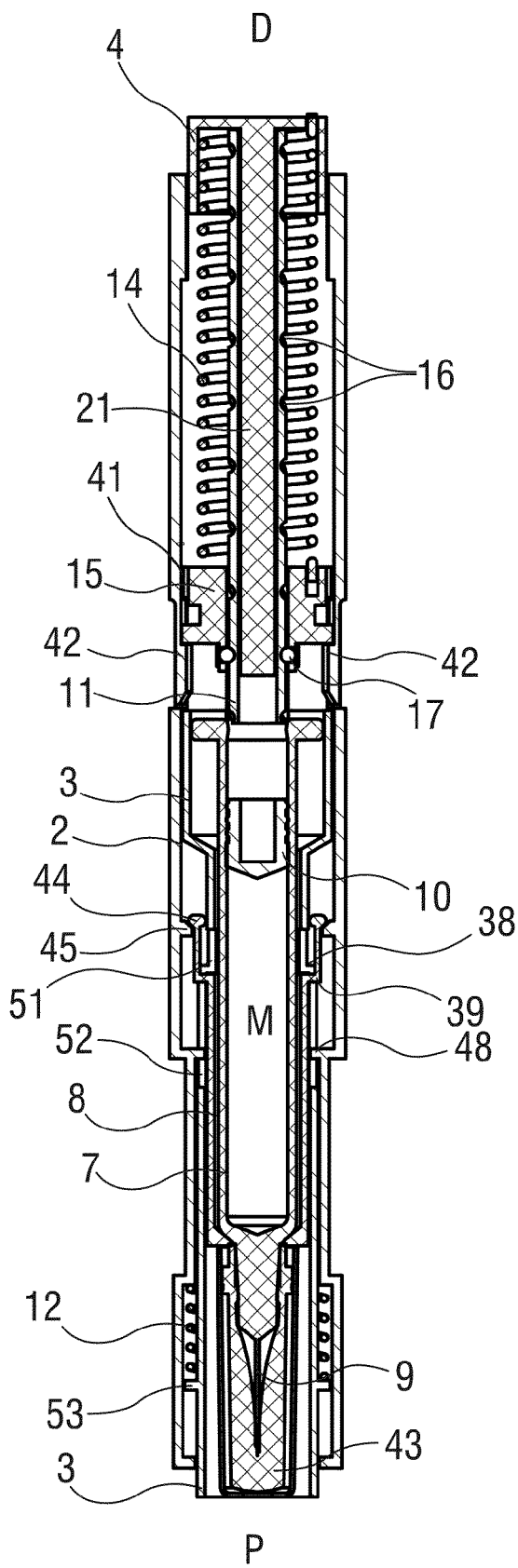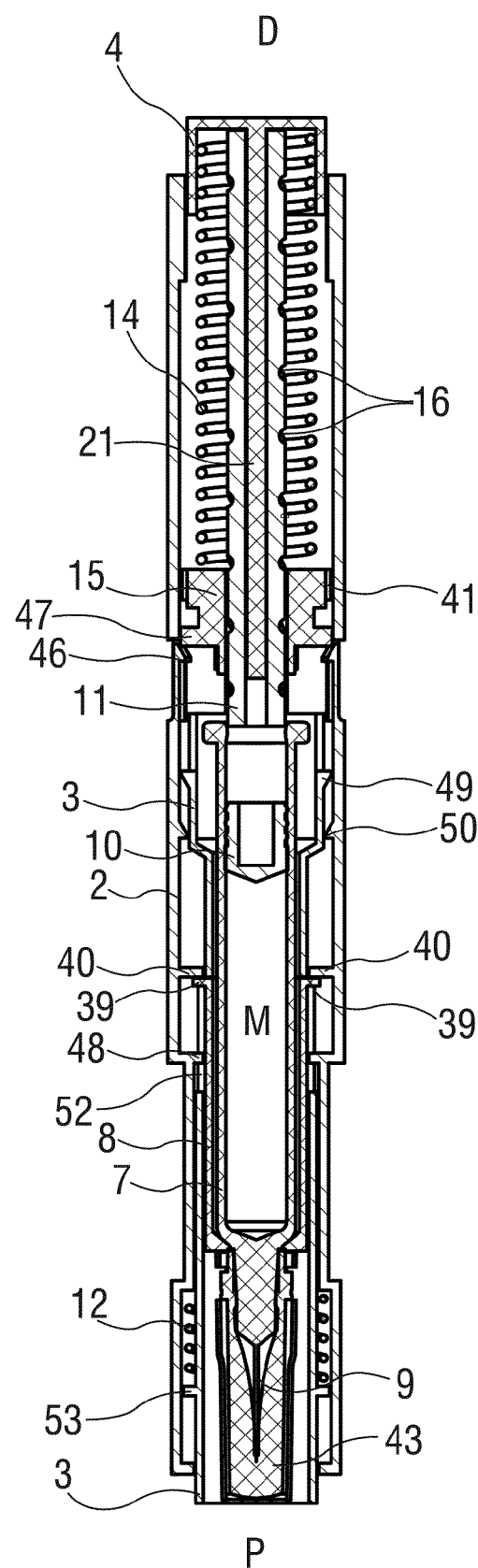

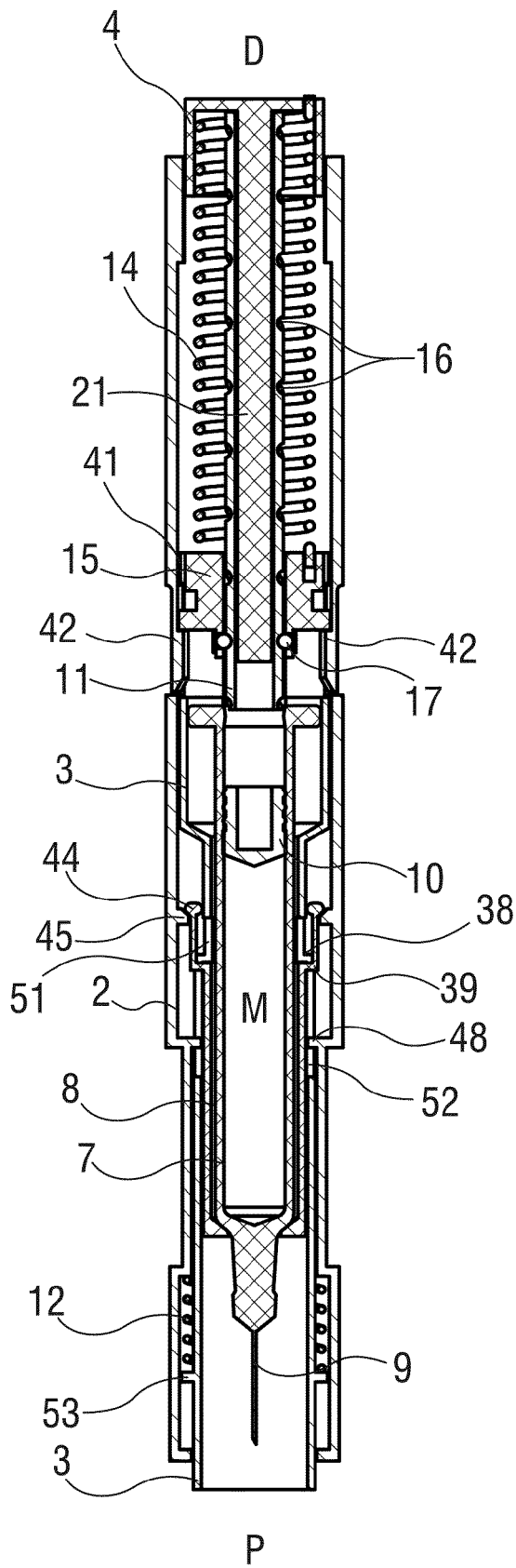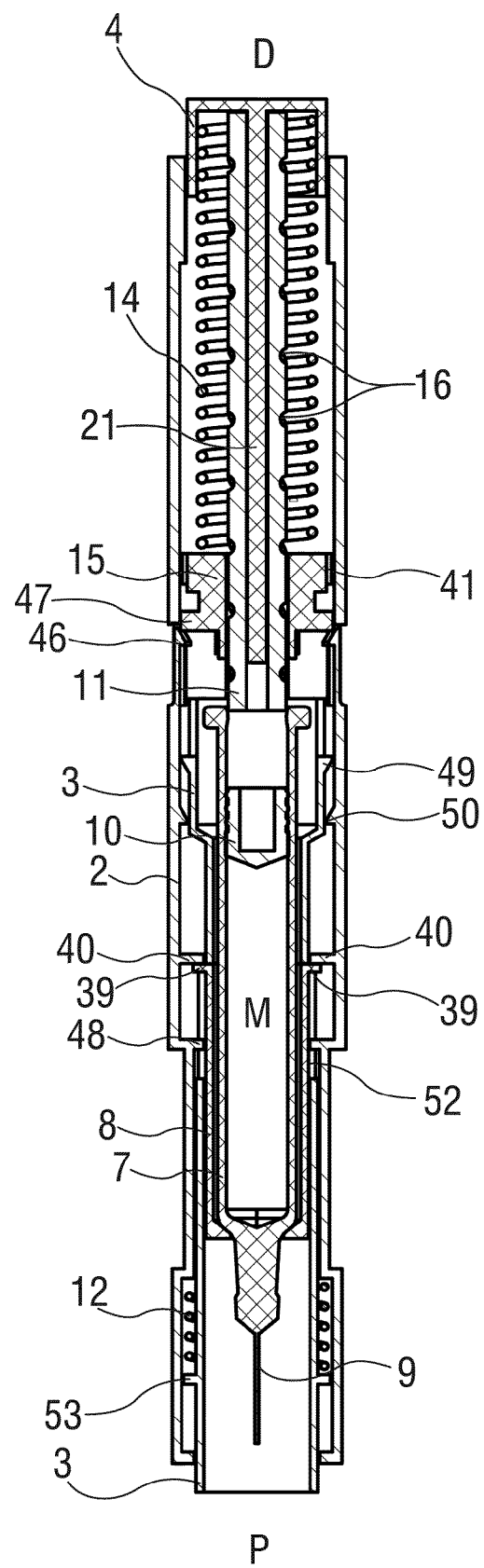

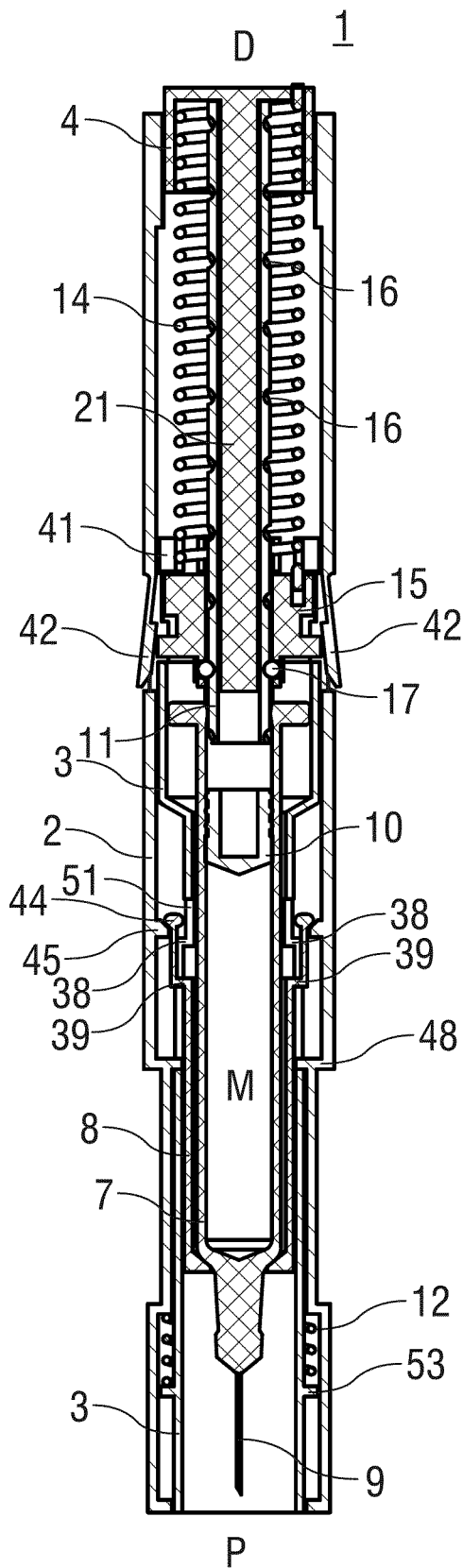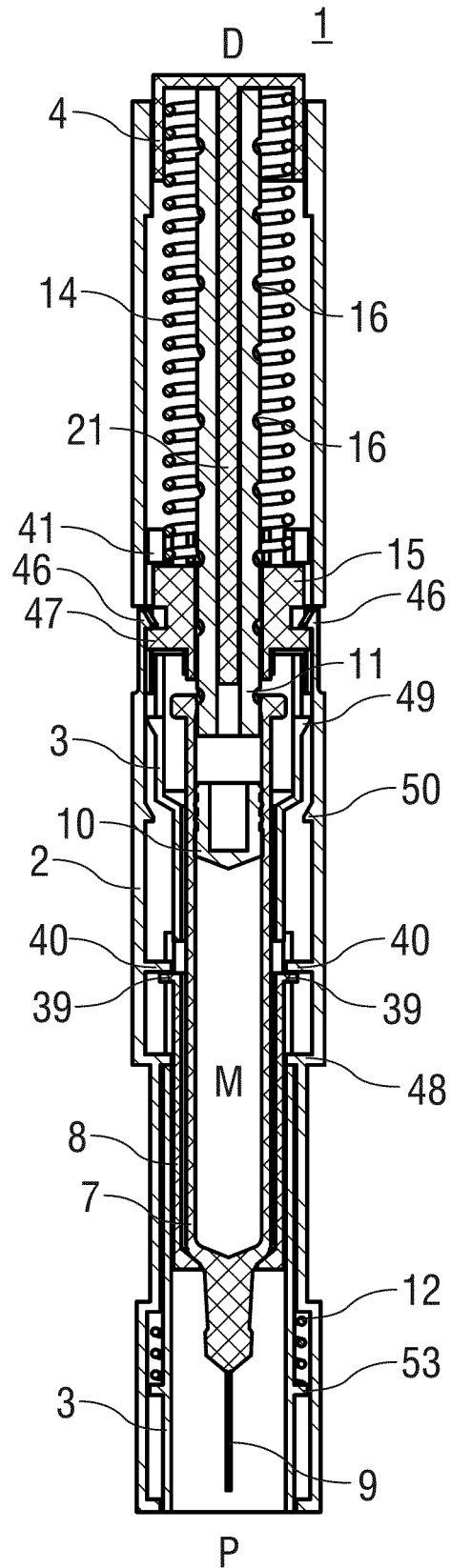
FIG 4A
FIG 4B

AUTO-INJECTOR

CROSS REFERENCE TO RELATED APPLICATIONS

The present application is a U.S. National Phase Application pursuant to 35 U.S.C. §371 of International Application No. PCT/EP2011/067490 filed Oct. 6, 2011, which claims priority to European Patent Application No. 10186991.5 filed Oct. 8, 2010 and U.S. Provisional Patent Application No. 61/432,262 filed Jan. 13, 2011. The entire disclosure contents of these applications are herewith incorporated by reference into the present application.

FIELD OF INVENTION

The invention relates to an auto-injector for administering a dose of a liquid medicament according to the preamble of claim 1.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

The European patent application EP 10153985.6 discloses an auto-injector for administering a dose of a liquid medicament, comprising:

an elongate housing arranged to contain a syringe with a hollow needle and a bung for sealing the syringe and displacing the medicament, the elongate housing having a distal end and a proximal end with an orifice intended to be applied against an injection site, wherein the syringe is slidably arranged with respect to the housing, spring means capable of, upon activation, pushing the needle from a covered position inside the housing into an advanced position through the orifice and past the proximal end as well as operating the syringe to supply the dose of medicament, activating means arranged to lock the spring means in a pressurized state prior to manual operation and capable of, upon manual operation, releasing the spring means for injection.

The spring means is a torsion spring grounded at one end in the housing and at the other end in a first gear member rotatable about a longitudinal axis but axially fixed. The first gear member, upon rotation, is arranged for translatively moving a second gear member. The second gear member is prevented from rotating and coupled to the bung in order to push it towards the proximal end. The first gear member is engaged with the activating means prior to manual operation in a manner to prevent rotation and disengaged from the activating means upon manual operation. When the torsion spring is released by operating the activating means the first gear member starts rotating.

SUMMARY

It is an object of the present invention to provide an improved auto-injector.

The object is achieved by an auto-injector according to claim 1.

Preferred embodiments of the invention are given in the dependent claims.

An auto-injector for administering a dose of a liquid medicament according to the invention comprises:

an elongate housing arranged to contain a syringe with a hollow needle and a bung for sealing the syringe and displacing the medicament, the elongate housing having a distal end and a proximal end with an orifice intended to be applied against an injection site, wherein the syringe is slidably arranged with respect to the housing, spring means capable of, upon activation, pushing the needle from a covered position inside the housing into an advanced position through the orifice and past the proximal end as well as operating the syringe to supply the dose of medicament, activating means arranged to lock the spring means in a pressurized state prior to manual operation and capable of, upon manual operation, releasing the spring means for injection.

In the context of this specification the term proximal refers to the direction pointing towards the patient during an injection while the term distal refers to the opposite direction pointing away from the patient.

According to the invention the spring means is a torsion spring grounded at one end in the housing and at the other end in a lead nut rotatable about a longitudinal axis but axially constrainable. The lead nut, upon rotation, is arranged for translatively moving a piston rod by means of a lead screw thread. The piston rod is prevented from rotating relative to the housing and coupled to the bung in order to push it towards the proximal end. The lead nut is engaged to the housing in an initial position prior to manual operation of the activating means in a manner to prevent it from rotating. Upon manual operation of the activating means the lead nut is disengaged from the housing. The torsion spring is preferably loaded or wound during manufacturing of the auto-injector.

The activating means is a trigger button arranged at a distal end of the housing and operable by being pressed in proximal direction. At least prior to manual operation the trigger button, the piston rod and the lead nut are coupled for joint translation in proximal direction. The lead nut is engaged to the housing by at least one spline feature in the initial position. The lead nut is arranged to disengage from the housing on translation in proximal direction from the initial position by sliding the spline feature out of a corresponding groove thus allowing it to rotate.

The single torsion spring is used for both, inserting the needle and fully emptying the syringe. A major advantage of the torsion spring and the gear consisting of the lead nut and the piston rod is that force is exerted on the bung and syringe in a smooth manner, whereas a conventional compression spring exhibits a rather abrupt force deployment which may spoil a glass syringe or other parts of the auto-injector.

In one embodiment an essentially tube-shaped needle shroud is arranged around the syringe in the housing. The needle shroud is slidable between at least a retracted position with the needle shroud almost hidden inside the housing and an advanced position with the needle shroud protruding from the proximal end and covering the hollow needle in its advanced position. The needle shroud is biased by a second spring means towards the advanced position. At least one latch is arranged in the housing for preventing the lead nut from translating from the initial position, e.g. by the lead nut abutting against that latch in proximal direction. The needle shroud is configured to flex the latch outwards on translation of the needle shroud from the retracted position by a small distance in distal direction so as to allow translation of the lead nut from the initial position in proximal direction. The needle shroud thus serves for enforcing a sequence of operation. Since the latch keeps the lead nut from advancing in proximal direction, the trigger button, which is coupled to the lead nut for joint translation in proximal direction, cannot be pushed. When the needle shroud is pushed by a small distance in distal direction from the retracted position by a user placing the proximal end of the auto-injector against an injection site, e.g. a patient's skin, the latch is released so the lead nut, the piston rod and the trigger button can translate in proximal direction, i.e. the button may be pressed. This sequence reduces the risk for inadvertently triggering the auto-injector. Another function of the needle shroud is to cover the needle after the injection. This makes the device safer than an equivalent manual injection with respect to post injection needle stick injuries.

The syringe may be arranged in a syringe carrier and supported by the syringe carrier at a proximal end. Supporting the syringe at its proximal end rather than at its flanges avoids damaging the syringe under load since the flanges are more fragile, in particular in a glass syringe. The syringe carrier may be slidably arranged in the needle shroud. The position of the needle shroud in proximal direction is limited by a shoulder in the needle shroud arranged for abutting against a carrier flange at the syringe carrier.

In one embodiment at least one wedge may be arranged on the syringe carrier. Prior to translation of the needle shroud from the retracted position in distal direction, i.e. prior to placing the auto-injector against the injection site, the wedge is caught between a second rib in the housing and the needle shroud so as to prevent the wedge and hence the syringe carrier from advancing in proximal direction. The needle shroud exhibits at least one aperture, which on translation of the needle shroud from the retracted position in distal direction moves next to the wedge so as to allow the wedge to flex into the aperture and release the syringe carrier for translation in proximal direction. Thus, the syringe and the needle cannot inadvertently be translated in a manner to expose the needle without properly positioning the needle shroud.

Preferably the trigger button may be splined to the housing. The piston rod may have an axial bore for slidably arranging the piston rod on a shaft attached to the trigger button, the axial bore and the shaft having corresponding non-circular profiles, e.g. square profiles or profiles with at least one spline or flat. Thus, the piston rod is prevented from rotating with respect to the housing.

At least one clip may be arranged for axially locking the lead nut to the housing on translation of the lead nut in proximal direction from the initial position. Once, engaged, the clip resolves any axial load applied to the piston rod in distal direction by axially constraining the lead nut.

In one embodiment the lead screw thread may have a variable pitch. Thus, speed and force of the needle insertion and injection of the medicament may be adapted to user convenience and to the fact that the torque of the torsion spring is highest when it is fully loaded and lowest near the end of the injection stroke. E.g. the pitch of the thread may be adapted to ensure a quick needle insertion and a relatively slow injection of the medicament in order to cause the least possible pain for the patient. The lead screw may be an external lead screw on the piston rod or an internal lead screw in the lead nut.

As the user withdraws the auto-injector from the injection site after the end of injection the needle shroud is pushed over the needle by the compression spring into its advanced position. A locking mechanism may be provided for locking the needle shroud in its advanced position so the needle cannot be re-exposed and needle stick injuries with the now contaminated needle are avoided.

The housing may have at least one viewing window for inspecting the syringe.

The lead nut may have an internal lead screw thread or a pin guided in the external lead screw thread of the piston rod. Preferably the lead nut is equipped with at least one ball bearing in order to achieve a low friction contact.

A lead nut flange may be arranged on the lead nut, the lead nut flange arranged to abut against the latch in the initial position and to be engaged by the clip on translation of the lead nut in proximal direction from the initial position.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1 are two longitudinal sections of an auto-injector with a torsion spring, a syringe with a needle, a needle shroud and a trigger button in a prior to use state, FIG. 2 are two longitudinal sections of the auto-injector after removal of a protective needle shield, FIG. 3 are two longitudinal sections of the auto-injector placed against an injection site, FIG. 4 are two longitudinal sections of the auto-injector with the trigger button pressed, FIG. 5 are two longitudinal sections of the auto-injector with the needle inserted into the injection site, FIG. 6 are two longitudinal sections of the auto-injector at the end of an injection stroke, and FIG. 7 are two longitudinal sections of the auto-injector with the needle shroud fully advanced and locked in forward position in order to protect the needle.

Corresponding parts are marked with the same reference symbols in all figures.

DETAILED DESCRIPTION

Figure 3A:
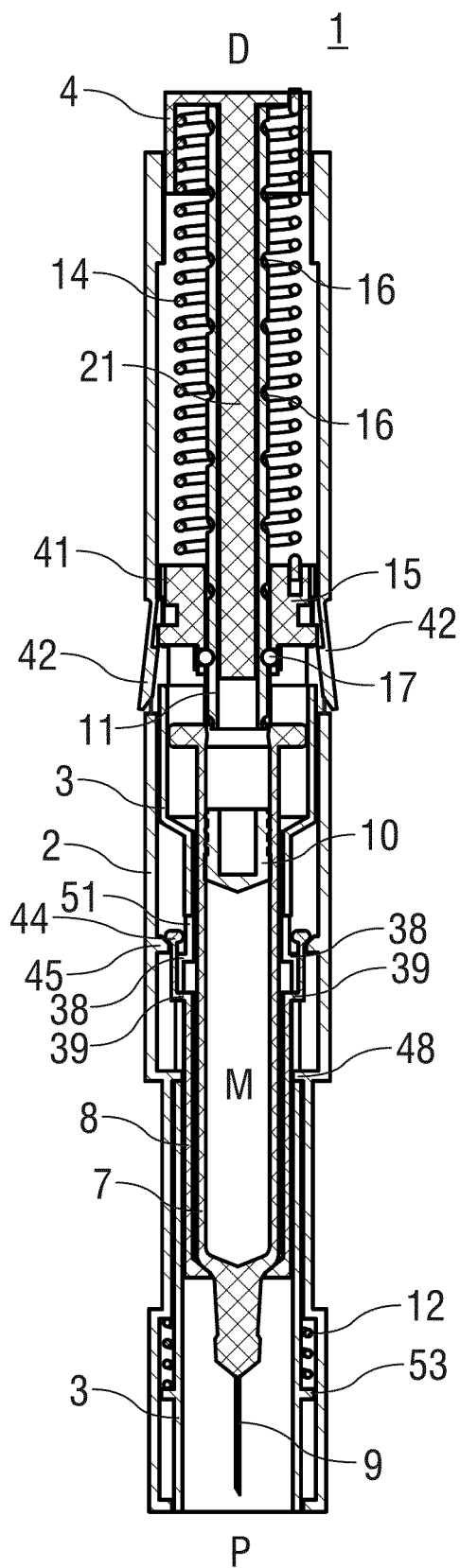

FIGS. 1a and 1b show two longitudinal section of an auto-injector 1 in two section planes which are about 90 degrees offset from each other. The auto-injector 1 comprises an elongate housing 2 and a needle shroud 3 for protecting a needle 9. A trigger button 4 arranged at a distal end of the auto-injector 1 may be depressed in proximal direction P in order to trigger an automatic injection. The trigger button 4 is interlocked with the needle shroud 3 so it cannot be pressed until the needle shroud 3 is pushed into the housing 2 by placing it on an injection site, e.g. a patient's skin and applying pressure. The needle shroud 3 has longitudinal splines engaged in corresponding grooves in the housing 1 for preventing relative rotation of the needle shroud 3 with respect to the housing 1.

FIGS. 1a and 1b show the auto-injector 1 in a prior to use state. A syringe 7 is partially surrounded and supported at a front end by a syringe carrier 8. The syringe carrier 8 is splined to the needle shroud 3 so as to prevent relative rotation. Since the needle shroud 3 is also splined to the housing 2, the syringe 7 and the needle 9 cannot rotate with respect to the housing 2. Attached at the front end of the syringe 7 is a hollow needle 9 for piercing a patient's skin and delivering a liquid medicament M stored inside the syringe 7. Near the distal end of the syringe 7 a bung 10 is arranged for sealing and containing the medicament. The bung 10 may be advanced by a piston rod 11 in order to expel the medicament M from the syringe 7. The syringe carrier 8 is slidably arranged inside the needle shroud 3. The needle shroud 3 is biased by a compression spring 12 towards a proximal end P. The position of the needle shroud 3 in proximal direction P is limited by a shoulder 38 in the needle shroud 3 that is in contact with a carrier flange 39 at the syringe carrier 8. The syringe carrier 8 is prevented from moving in distal direction D by the carrier flange 39 contacting a first rib 40 in the housing 2. Translation of the syringe carrier 8 in proximal direction P is prevented by a wedge 44 on the syringe carrier 8 caught between a second rib 45 in the housing 2 and the needle shroud 3.

A torsion spring 14 is arranged near a distal end D of the auto-injector 1 inside the housing 2. A distal end of the torsion spring 14 is attached to the trigger button 4 which is rotationally constrained to the housing 2 through a spline (not illustrated) so torque from the torsion spring 14 is reacted into the housing 2. The other, proximal end of the torsion spring 14 is coupled to a lead nut 15 which is rotatably mounted around a piston rod 11. The piston rod 11 has an external lead screw thread 16 engaged with the lead nut 15. The lead nut 15 is equipped with at least one ball bearing 17 for this engagement. It could alternatively have at least one pin. In the prior to use state shown in FIGS. 1a and 1b the lead nut 15 is biased by the torsion spring 14 but kept from rotating by a spline feature 41 to the housing 2. Furthermore, the lead nut 15 is kept from moving in proximal direction P by a lead nut flange 47 abutting against a latch 42 in the housing 2. The piston rod 11 is guided along a shaft 21 arranged in an axial bore of the piston rod 11. The axial bore and the shaft 21 both have a non-circular profile in order to keep the piston rod 11 from rotating, e.g. a square profile or a profile with at least one spline or flat. The shaft 21 is attached to the trigger button 4 which is rotationally constrained with respect to the housing 2.

A protective needle shield 43 is provided on the hollow needle 9. The protective needle shield 43 has to be removed prior to use by a user resulting in the situation illustrated in FIGS. 2a and 2b. In this situation the needle 9 is a safe distance back within the needle shroud 3 to protect the user from accidental needlestick injuries. Rotation of the needle 9 is prevented by a spline between the housing 2 and the syringe carrier 8 (not illustrated), and by the non-circular flange of the syringe 7 (not illustrated) mating with a similarly shaped recess in syringe carrier 8. Any axial load applied to the syringe carrier 8 is resolved through the interlock comprising the wedge 44, the second rib 45 and the needle shroud 3 described above.

Figure 3B:
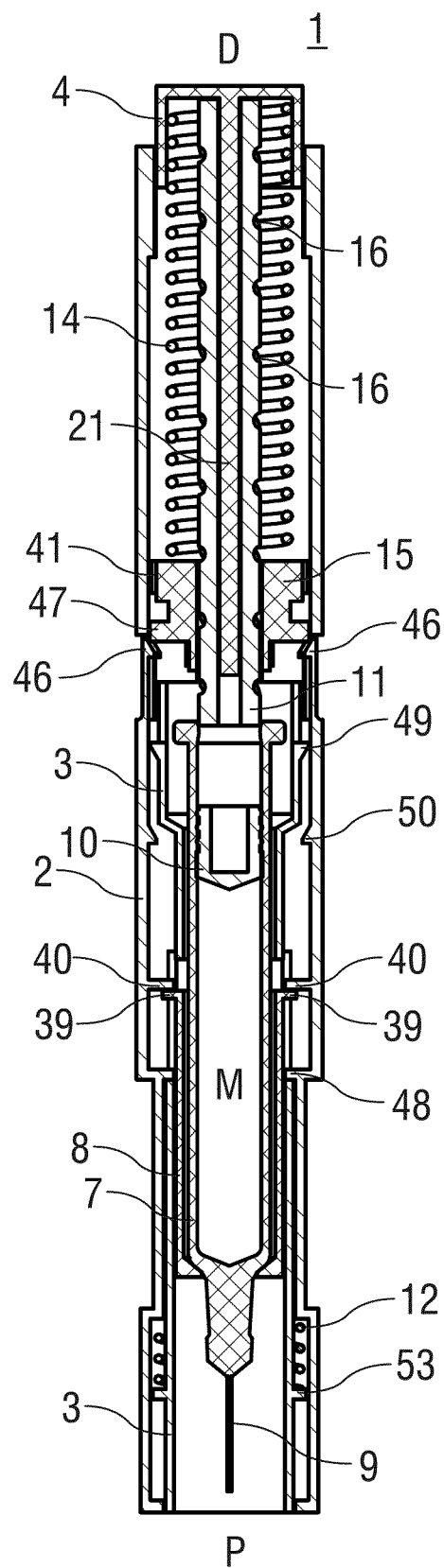

In order to prepare for an injection the user pushes the proximal end P of the auto-injector 1 against the injection site. Thus the needle shroud 3 is moved into the auto-injector 1 by a small distance (see FIGS. 3a and 3b) thereby removing it from the wedge 44 which can now flex into a first aperture 51 in the needle shroud 3 thus freeing the syringe carrier 8 to advance in proximal direction P. A distal end of the needle shroud 3 is arranged to flex the latches 42 outwards thus freeing the lead nut 15 to advance in proximal direction P. Movement of the needle shroud 3 in the distal direction D is limited by the end of a second aperture 52 in shroud 3 contacting the proximal face of a third rib 48 in the housing 2.

The compression spring 12 opposes the motion of the needle shroud 3 but is specified such that its spring rate and preload are low enough to feel natural for the user. The trigger button 4 may now be operated.

When ready to do so, the user pushes the trigger button 4 in proximal direction P (see FIGS. 4a and 4b). Since the piston rod 11 abuts against the trigger button 4, pushing the trigger button 4 moves the trigger button 4, the piston rod 11, the ball bearings 17 and the lead nut 15 in proximal direction P as one assembly. As the lead nut 15 moves in proximal direction P relative to the housing 2, the spline features 41 between the lead nut 15 and the housing 2 disengage, thus releasing the lead nut 15. Torque from the torsion spring 14 is now resolved through the ball bearings 17, the lead screw thread 16, the piston rod 11 onto the shaft 21. The lead nut 15 is moved in proximal direction P by the trigger button 4 until clips 46 in the housing 2 snap over the lead nut flange 47. These clips 46 resolve any axial load applied to the piston rod 11 in distal direction D.

Figure 5A:
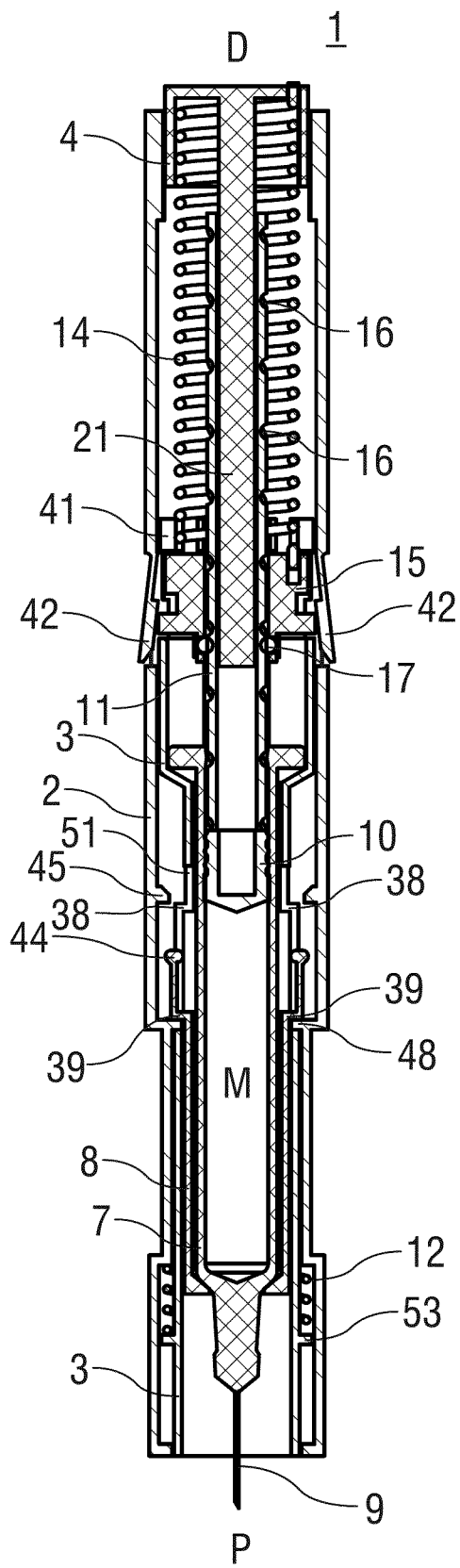
Figure 5B:
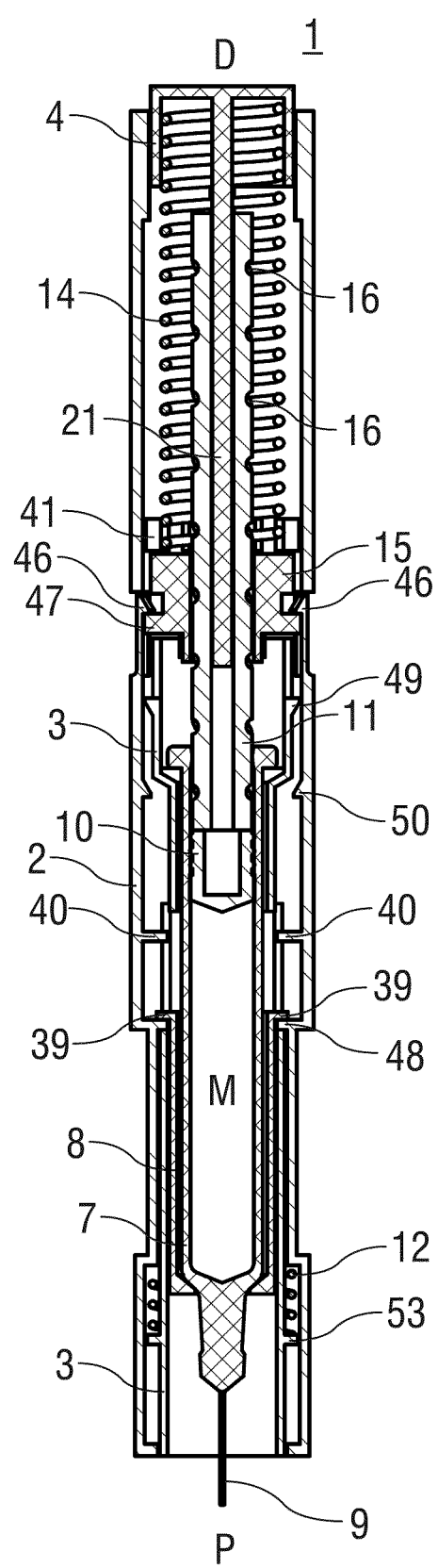

As shown in FIGS. 5a and 5b, the piston rod 11, kept from rotating by the shaft 21, is pushed forward in proximal direction P due to the engagement of the lead nut 15 and the lead screw thread 16. The advancing piston rod 11 pushes against the bung 10 which in turn advances the syringe 7 by virtue of the friction between the bung 10 and the syringe wall and due to the thin fluid channel inside the hollow needle 9 opposing the displacement of the medicament M. The advancing syringe 7 also causes the needle 9 to protrude beyond the proximal end P of the auto-injector 1 into the injection site, e.g. the patient's skin. Since the syringe 7 is supported at its proximal end by an orifice of the syringe carrier 8 the syringe carrier 8 is also advanced with the syringe 7 until the carrier flange 39 abuts against a third rib 48 in the housing 2. This contact sets the injection depth relative to the housing 2.

After the carrier flange 39 has hit the third rib 48 the syringe 7 is kept from advancing further. The load from the bung 10 is resolved through the piston rod 11, into the lead nut 15 and then into the housing 2 through the clips 46. With the lead nut 15 still rotating and pushing the piston rod 11 the bung 10 overcomes the friction and the hydraulic resistance of the medicament M and advances inside the syringe 7 thereby displacing the medicament M and delivering it through the fluid channel of the hollow needle 9 into or through the patient's skin.

Figure 6A:
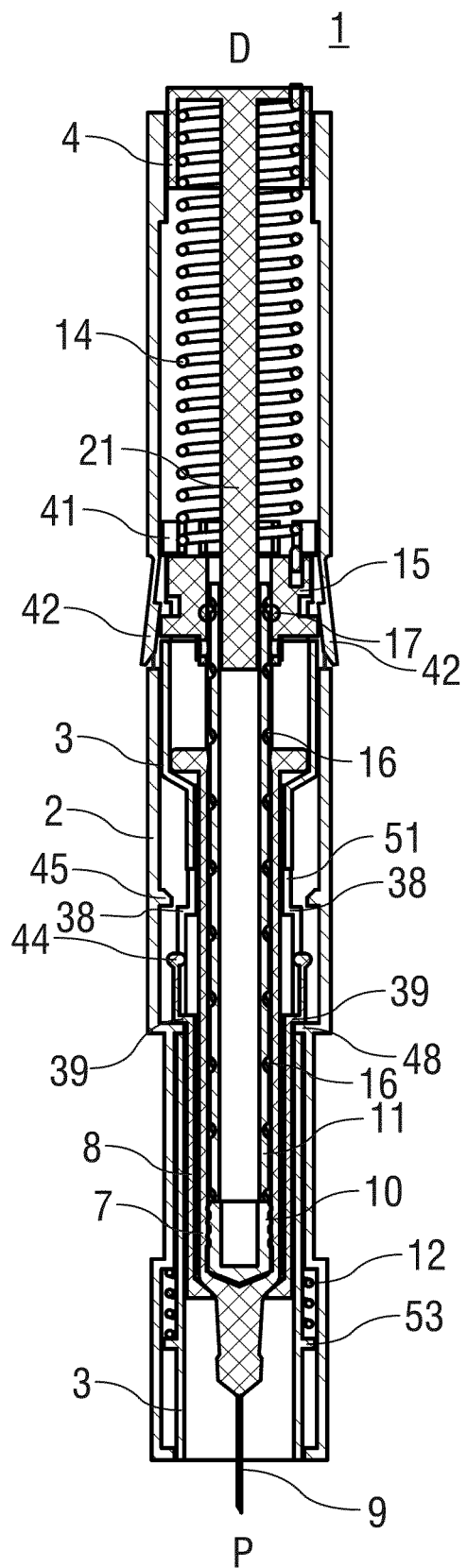
Figure 6B:
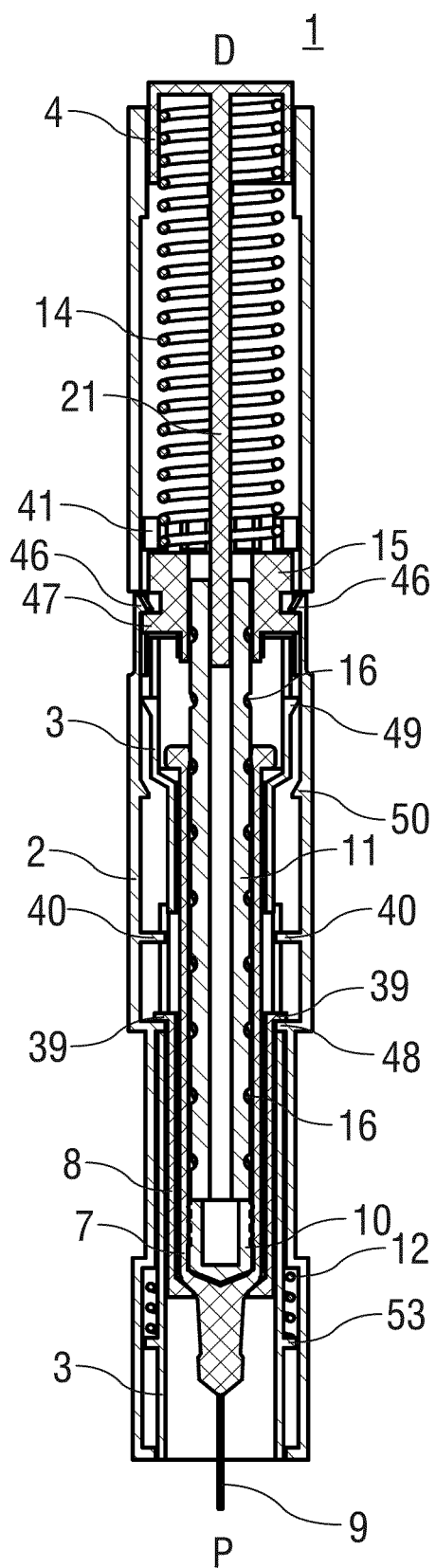

FIGS. 6a and 6b show the piston rod 11 and the bung 10 almost fully advanced and the syringe 7 emptied. The user would be asked to keep pressure with the auto-injector 1 at the injection site for a short period of time (e.g. ten seconds) to ensure this is achieved.

Figure 7A:
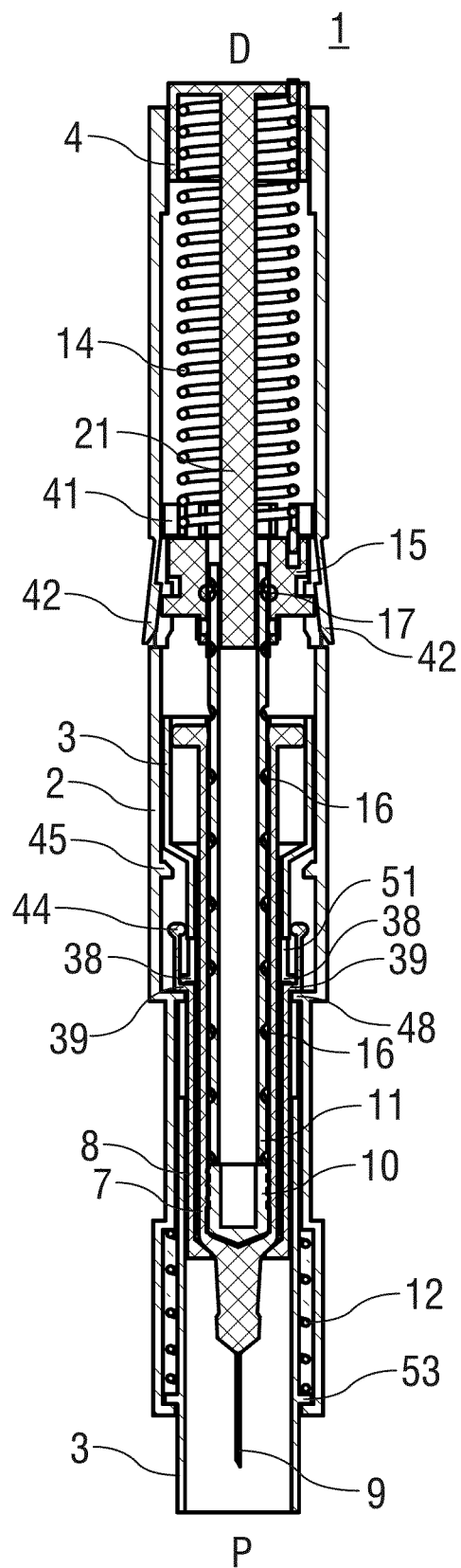
Figure 7B:
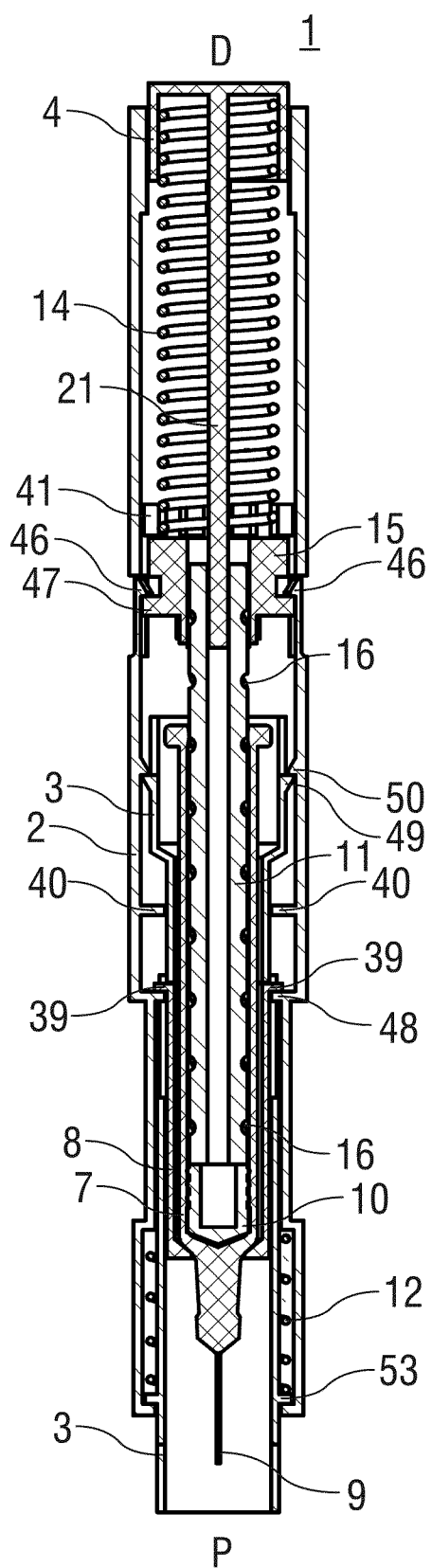

As the user withdraws the auto-injector 1 from the injection site the needle shroud 3 is pushed over the needle 9 in proximal direction P by the compression spring 12. This situation is shown in FIGS. 7a and 7b. The proximal position of the needle shroud 3 is limited by the shoulder 38 in the needle shroud 3 abutting against the carrier flange 39 as in the initial prior to use state illustrated in FIG. 1, and by a shroud flange 53 on the needle shroud 3 in contact with the proximal end of the compression spring 12 coming into contact with the extreme proximal end of housing 2. The syringe carrier 8 is now positioned further in proximal direction P hence the needle shroud 3 protrudes further from the proximal end P of the housing 2 than in the initial state.

As the needle shroud 3 is advanced in proximal direction P by the compression spring 12 a resilient snap feature 49 in the needle shroud 3 passes a ramp 50 in the case and locks the needle shroud 3 in this forward position in order to prevent re-exposure of the needle 9.

If the user were to remove the auto-injector 1 from the skin prior to full syringe emptying, the described motion of the needle shroud 3 would still be achieved A viewing window may be arranged for viewing and inspecting the syringe 7 held in the auto-injector 1.

The auto-injector 1 may preferably be used for delivering one of an analgetic, an anticoagulant, insulin, an insulin derivate, heparin, Lovenox, a vaccine, a growth hormone, a peptide hormone, a proteine, antibodies and complex carbohydrates.

The invention claimed is:

1. Auto-injector for administering a dose of a liquid medicament, comprising:
   an elongate housing arranged to contain a syringe with a hollow needle and a bung for sealing the syringe and displacing the medicament, the elongate housing having a distal end and a proximal end with an orifice intended to be applied against an injection site, wherein the syringe is slidably arranged with respect to the housing,
   spring means capable of, upon activation, pushing the needle from a covered position inside the housing into an advanced position through the orifice and past the proximal end as well as operating the syringe to supply the dose of medicament,
   activating means arranged to lock the spring means in a pressurized state prior to manual operation and capable of, upon manual operation, releasing the spring means for injection,
   wherein the spring means is a torsion spring grounded at one end in the housing and at the other end in a lead nut rotatable about a longitudinal axis but axially constrainable, wherein the lead nut, upon rotation, is arranged for translatively moving a piston rod by means of a lead screw thread, the piston rod being prevented from rotating relative to the housing and arranged to be coupled to the bung in order to push it towards the proximal end, wherein the lead nut is engaged to the housing in an initial position prior to manual operation of the activating means in a manner to prevent rotation and disengaged from the housing by the activating means upon manual operation,
   characterized in that the activating means is a trigger button, arranged at a distal end of the housing and operable by being pressed in proximal direction, wherein at least prior to manual operation the trigger button, the piston rod and the lead nut are coupled for joint translation in proximal direction, wherein the lead nut is engaged to the housing by at least one spline feature in the initial position and wherein the lead nut is arranged to disengage from the housing on translation in proximal direction from the initial position.

2. Auto-injector according to claim 1, characterized in that an essentially tube-shaped needle shroud is arranged around the syringe in the housing, the needle shroud slidable between at least a retracted position with the needle shroud almost hidden inside the housing and an advanced position with the needle shroud protruding from the proximal end and covering the hollow needle in its advanced position, wherein the needle shroud is biased by a second spring means towards the advanced position, wherein at least one latch is arranged in the housing for preventing the lead nut from translating from the initial position, wherein the needle shroud is configured to flex the latch outwards on translation of the needle shroud from the retracted position in distal direction so as to allow translation of the lead nut from the initial position in proximal direction.

3. Auto-injector according to claim 2, characterized in that the syringe is arranged in a syringe carrier and supported by the syringe carrier at a proximal end, wherein the syringe carrier is slidably arranged in the needle shroud, wherein the position of the needle shroud in proximal direction is limited by a shoulder in the needle shroud that is in contact with a carrier flange at the syringe carrier.

4. Auto-injector according to claim 3, characterized in that at least one wedge is arranged on the syringe carrier, wherein prior to translation of the needle shroud from the retracted position in distal direction the wedge is caught between a second rib in the housing and the needle shroud so as to prevent the syringe carrier from advancing in proximal direction, wherein the needle shroud exhibits at least one aperture, which on translation of the needle shroud from the retracted position in distal direction moves next to the wedge so as to allow the wedge to flex into the aperture and release the syringe carrier for translation in proximal direction.

5. Auto-injector according to claim 1, characterized in that the trigger button is splined to the housing, wherein the piston rod has an axial bore for slidably arranging the piston rod on a shaft attached to the trigger button, the axial bore and the shaft having corresponding non-circular profiles.

6. Auto-injector according to claim 1, characterized in that at least one clip is arranged for axially locking the lead nut to the housing on translation of the lead nut in proximal direction from the initial position.

7. Auto-injector according to claim 1, characterized in that the lead screw thread has a variable pitch.

8. Auto-injector according to claim 2, characterized in that a locking mechanism is provided for locking the needle shroud in its advanced position.

9. Auto-injector according to claim 1, characterized in that at least one viewing window for inspecting the syringe is provided in the housing.

10. Auto-injector according to claim 1, characterized in that at least one pin or at least one ball bearing is arranged between the lead nut and the piston rod for engaging the lead screw thread.

11. Auto-injector according to claim 6, characterized in that a lead nut flange is arranged on the lead nut, the lead nut flange arranged to abut against the latch in the initial position and to be engaged by the clip on translation of the lead nut in proximal direction from the initial position.

* * * * *